US007045617B2

(12) United States Patent
Cole et al.

(10) Patent No.: US 7,045,617 B2
(45) Date of Patent: May 16, 2006

(54) BISBUBSTRATE INHIBITORS OF KINASES

(75) Inventors: Philip A. Cole, Baltimore, MD (US); Keykavous Parang, Narragansett, RI (US); Ararat Abloogu, New York, NY (US); Ronald A. Kohanski, Fair Lawn, NJ (US); Aliya Courtney, Baltimore, MD (US)

(73) Assignees: Mount Sinai School of Medicine, New York, NY (US); Johns Hopkins University, Baltimore, MD (US)

(*) Notice: Subject to any disclaimer, the term of this patent is extended or adjusted under 35 U.S.C. 154(b) by 587 days.

(21) Appl. No.: 09/811,870

(22) Filed: Mar. 21, 2001

(65) Prior Publication Data

US 2002/0031820 A1    Mar. 14, 2002

Related U.S. Application Data

(60) Provisional application No. 60/190,799, filed on Mar. 21, 2000.

(51) Int. Cl.
*C07H 19/20*    (2006.01)
*A61K 38/28*    (2006.01)
*A61K 38/00*    (2006.01)
*A61K 38/04*    (2006.01)

(52) U.S. Cl. .................... 536/26.26; 530/303; 530/326

(58) Field of Classification Search ............... 530/323, 530/300; 435/194; 536/26.13; 514/2
See application file for complete search history.

(56) References Cited

U.S. PATENT DOCUMENTS 4,962,155 A * 10/1990 Fujita-Yamaguchi et al. .... 525/54.1
5,922,844 A *  7/1999 Hawkins et al. ............ 530/350
5,990,094 A    11/1999 Cole et al. .................... 514/47

OTHER PUBLICATIONS

Loog et al. (1999) Bioorg Med Chem Lett 9:1447-1452.*
Ricouart; "*Design of Potent Protein Kinase Inhibitors Using the Bisubstrate approach*"; Journal of Medical Chemistry, American Chemical Society; vol. 34, No. 1, 1991, pp. 73-78.
S. R. Hubbard; "*Crystal Structure of the Activated Insulin Receptor Tyrosine Kinase in Complex with Peptide Substrate and ATP Analog*"; The EMBO Journal, vol. 16, No. 18, 1997, pp. 5572-5581.
Denes Medzihradszky et al., "*Solid-Phase Synthesis of Adenosine Phosphopeptides as Potential Bisubstrate Inhibitors of Protein Kinases*", Journal of the American Chemical Society; vol. 116, No. 21, 1994, pp. 9413-9419.
Gérard Rossé et al., "*Synthesis of Modified Tripeptides and Tetrapeptides as Potential Bisubstrate Inhibitors of the Epidermal Growth Factor Receptor Protein Tyrosine Kinase*", Helvetica Chimica ACTA, (1997), 80(3), pp. 653-670.
E. A. Kim, "*Kinetic Analysis of a Protein Tyrosine Kinase Reaction Transition State in the Forward and Reverse Directions*", Journal of the American Chemical Society, vol. 120, No. 28, Jul. 1998, pp. 6851-6858.
International Search Report for PCT/US01/08886 (WO 01/70770).
K. Parang et al., "Mechanism-based Design of a Protein Kinase Inhibitor", Jan. 2001, Nature Structural Biology, vol. 8, No. 1, pps. 37-41.
W. Miller, "Double Trouble", Nature Structural Biology, vol. 8, No. 1, Jan. 2001, pps. 16-18.
D. Lawrence et al., "Protein Kinase Inhibitors: The Tyrosine-Specific Protein Kinases", Pharmacol. Ther., vol. 77, No. 2, 1998, pps. 81-114.
S. Basu et al., "Synthesis and Characterization of a Peptide Nucleic Acid Conjugated to a D-Peptide Analog of Insulin-Like Growth Factor 1 for Increased Cellular Uptake", Biconjug. Chem 8:481-8 (1997); abstract only.
R. Arav et al., "Combined Effects of ATP and Its Analogs on the Membrane Permeability in Transformed Mouse Fibroblasts", FEBS Lett 387:149-151 (1996); abstract only.
P. Wittung et al., "Phospholipid Membrane Permeability of Peptide Nucleic Acid", FEBS Lett 365: 27-29 (1995); abstract only.

* cited by examiner

Primary Examiner—David J. Steadman
(74) Attorney, Agent, or Firm—Banner & Witcoff, Ltd.

(57) ABSTRACT

Protein kinase inhibitors have applications as anti-cancer therapeutic agents and biological tools in cell signalling. Potent and selective bisubstrate inhibitors for the insulin receptor tyrosine kinase are based on a phosphoryl transfer mechanism involving a dissociative transition state. One such inhibitor is synthesized by linking ATPγS to a peptide substrate analog via a two-carbon spacer. The compound is a high-affinity competitive inhibitor against both nucleotide and peptide substrate and shows a slow off-rate. A crystal structure of this inhibitor bound to the tyrosine kinase domain of the insulin receptor confirms the key design features inspired by a dissociative transition state, and reveal that the linker takes part in the octahedral coordination of an active site $Mg^{2+}$ ion.

1 Claim, 6 Drawing Sheets

Inhibition assay for protein kinase A.
Final concentrations for reaction components : ATP = 15 uM,
kemptide = 25 uM, Mg2+ = 10mM, Tris-HCl = 40 mM,
bovine serum albumin (from enzyme mix) 150 ug/mL.
All reactions were carried out at pH 7.5 and with a
final enzyme concentration of 0.35 nM
for 2 minutes at 30 degrees Celsius.

R'=CH2CO-peptide or peptidomimetic

R=adenosine or nucleoside analog n=0-6 n=0-6 n=0-6

X=O, NH, S, CH2
Y=O, NH, S, CH2

X=O, NH, S, CH2    n=0-6 n=0-6

US 7,045,617 B2

BISBUBSTRATE INHIBITORS OF KINASES

This application claims priority to provisional U.S. Application Ser. No. 60/190,799, filed Mar. 21, 2000, the disclosure of which is expressly incorporated herein.

This invention was made under terms of grant CSK/NIH/R29CA74305 from the U.S. National Institutes of Health. The U.S. government therefore retains certain rights in the invention.

FIELD OF THE INVENTION

The invention relates to the development of highly specific inhibitors for kinase enzymes which are involved in processes including inflammation, cancer, cardiovascular disease, endocrine disorders, immunomodulators, Alzheimer's disease, diabetes, and restenosis.

BACKGROUND OF THE INVENTION

Protein kinases play a critical role in cell signalling pathways by catalyzing transfer of the γ-phosphoryl group from ATP to the hydroxyl groups of protein side chains[1]. Approximately 2% of eukaryotic genes encode protein kinases making this one of the largest protein superfamilies. Because of their importance in contributing to a variety of pathophysiologic states including cancer, inflammatory conditions, autoimmune disorders, and cardiac diseases, there have been intense efforts to develop specific protein kinase inhibitors as biological tools and as therapeutic agents[2]. Considerable success has been achieved developing potent and selective nucleotide-based analog inhibitors that interact with individual protein kinases at their nucleotide binding sites, and several compounds are in early phases of human clinical trials[2]. In general, the protein substrate binding site has not been exploited for inhibitor design[3]. Moreover, mechanism-based approaches to generating protein kinase inhibitors have been unsuccessful[4-8]. This situation stands in contrast to many other important enzyme classes, such as the proteases, where consideration of enzyme mechanism and structure has led to potent inhibitors, some of which are clinically useful drugs[9].

Protein kinases follow ternary complex kinetic mechanisms in which direct transfer of the phosphoryl group from ATP to protein substrate occurs[10]. For such mechanisms, designing covalently linked bisubstrate analogs can be a powerful approach toward potent enzyme inhibitors[9]. However, previous attempts to employ this strategy with protein kinases have met with mixed results[4, 8, 11]. A sophisticated effort reported by Gibson and colleagues linked ATP directly to the serine oxygen of a protein kinase A (PKA) peptide substrate (kemptide) to generate an inhibitor (1, FIG. 1a)[8]. Compound 1 was a weak inhibitor with an IC50 of 226 mM (compared to Km (ATP) of 10 mM and Km (kemptide) of 15 mM) which was competitive versus ATP but non-competitive versus peptide substrate. While not providing all the desired features of a bisubstrate analog, these results suggest that improvements in geometry and electronic character around the atoms equivalent to the entering nucleophile and reacting phosphate would benefit inhibitor design. There is a need in the art for kinase inhibitors which are stronger than those currently available.

BRIEF SUMMARY OF THE INVENTION

In a first embodiment of the invention a bisubstrate inhibitor of insulin receptor kinase is provided. The inhibitor comprises a nucleotide or nucleotide analog moiety and a peptide moiety. The moieties are linked by a tether that comprises a proton donor. The tether is ≧4.9 Å measured from a gamma phosphorus of the nucleotide or nucleotide analog moiety to the proton donor.

In a second embodiment of the invention a method of inhibiting insulin receptor kinase (IRK) is provided. IRK is contacted with a bisubstrate inhibitor which comprises a nucleotide or nucleotide analog moiety and a peptide moiety. The two moieties are linked by a tether that comprises a proton donor. The tether is ≧4.9 Å measured from a gamma phosphorus of the nucleotide or nucleotide analog to the proton donor, whereby the IRK is competitively inhibited.

In another embodiment of the invention a bisubstrate inhibitor of protein kinase A (PKA) is provided. The inhibitor comprises a nucleotide or nucleotide analog moiety and a peptide moiety. The moieties are linked by a tether that comprises a proton donor. The tether is ≧4.9 Å measured from a gamma phosphorus of the nucleotide or nucleotide analog to the proton donor.

In still another embodiment of the invention a method is provided for inhibiting protein kinase A (PKA). A bisubstrate inhibitor is contacted with PKA. The inhibitor comprises a nucleotide or nucleotide analog moiety and a peptide moiety. The moieties are linked by a tether that comprises a proton donor and which is ≧4.9 Å measured from a gamma phosphorus of the nucleotide or nucleotide analog to the proton donor. The inhibitor competitively inhibits the PKA enzyme.

In yet another embodiment of the invention a bisubstrate inhibitor of a protein kinase is provided. The inhibitor comprises a nucleotide or nucleotide analog moiety and a peptide moiety. The two moieties are linked by a tether that comprises a proton donor, wherein the tether is ≧4.9 Å measured from a gamma phosphorus of the nucleotide or nucleotide analog to the proton donor. The inhibitor can be contacted with the kinase to inhibit the enzyme activity.

The invention thus provides the art with inhibitory compounds and methods of inhibiting protein kinases, including the serine kinases, the threonine kinases, and the tyrosine kinases. In addition, the invention provides a general method of designing bisubstrate inhibitors for other kinases based on the dissociative transition state.

$v=V_m(S)/[K_m(1+I/K_i)+S]$; v=initial velocity, $V_m$=maximal velocity, S=substrate concentration, $K_m$=Michaelis constant. For a, apparent $K_i(2)=550\pm80$ nM, for b, apparent $K_i(2)=750 \pm90$ nM. Inclusion of a $K_i$-intercept term (for a mixed competitive inhibition calculation) for either analysis did not reduce standard errors in the global fit and led to very high standard errors for the $K_i$-intercept terms, thereby adding confidence to our selection of linear competitive inhibition for a and b. c, Product/Enzyme versus Time. This experiment monitors the product formation after a rapid dilution of the enzyme/inhibition complex to indirectly measure the $k_{off}$ of 2 from IRK. Conditions: Incubation of 1 mM IRK +/–5 mM 2 for 10 min in reaction buffer (20 mM $MgCl_2$, 0.5 mM DTT, 0.05% BSA, 50 mM Tris-Acetate, pH 7) then dilute 1:50 into reaction buffer containing 1 mM ATP and 250 mM peptide6 IRS939 and measure conversion by HPLC at times shown. To determine $k_{off}$, data were fit to the equation[17]:

$P=vs*(t-[1-e-k_{off}t])/k_{off}$; P=Product concentration, vs=steady-state velocity, t=time and koff is the first-order rate constant for dissociation of 2 from the enzyme. $k_{off}=0.013\pm0.001$ s$^{-1}$.

Figure 3:
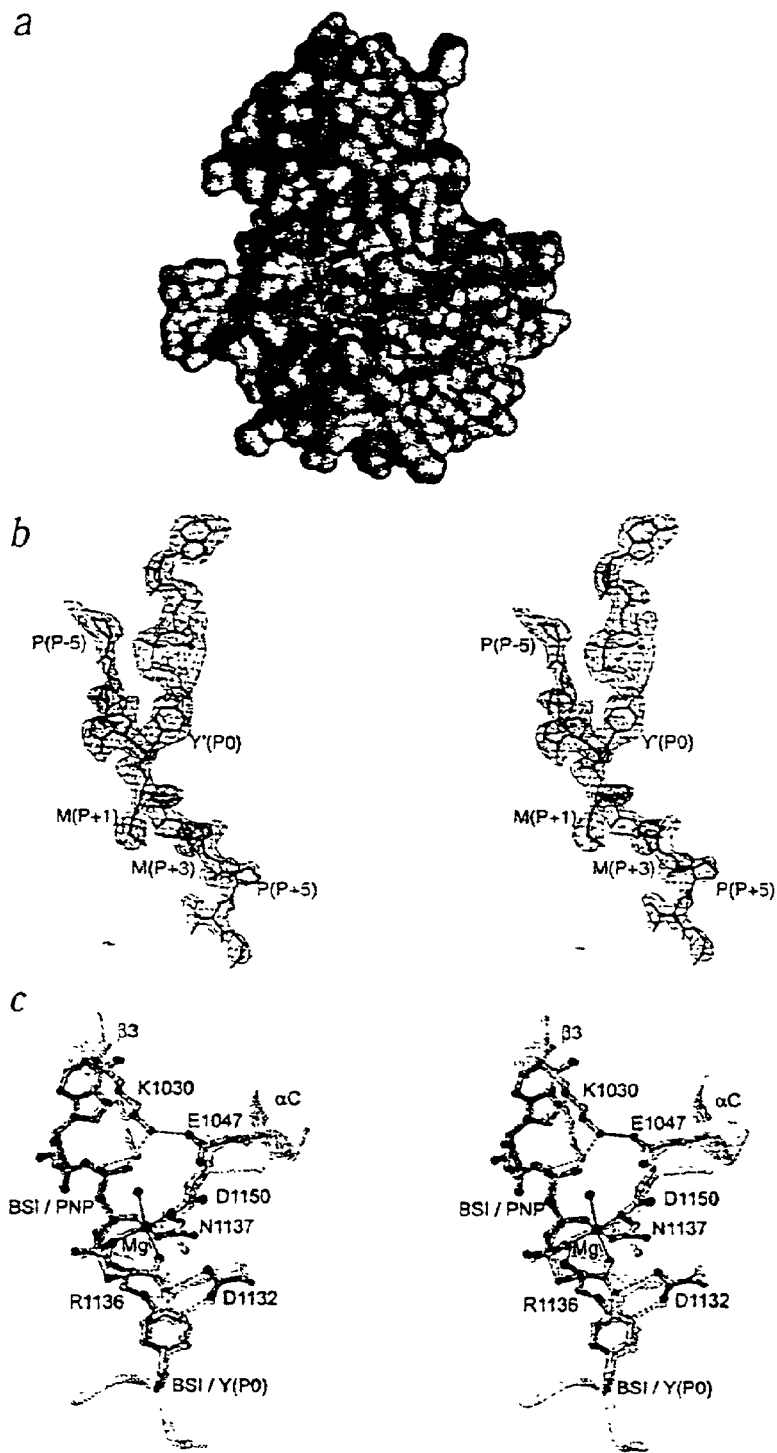

FIG. 3 Crystal structure of the binary complex between cIRK and the bisubstrate inhibitor. a, Overall view of the binary complex in which cIRK is shown in surface representation and the bisubstrate inhibitor in stick representation. The ATPγS moiety of the inhibitor is colored green, the peptide moiety is colored red, and the linker connecting the nucleotide and peptide is colored yellow. The cIRK surface is semi-transparent; the N-terminal lobe of cIRK partially masks the nucleotide. b, Stereo view of the Fo-Fc electron density (2.7 Å resolution, 3s contour) for the bisubstrate inhibitor computed after simulated annealing (1000K), omitting from the atomic model either ATPγS+linker (blue map) or the peptide moiety (green map). Coloring of the bisubstrate inhibitor is the same as in a. Selected peptide residues are labeled; Y'(P0) refers to the modified tyrosine at the P0 position of the peptide. The purple sphere represents the Mg2+ ion and the red sphere represents the Mg2+-coordinating water molecule. c, Stereo view of the interactions between the inhibitor and key catalytic residues. Superimposed are the cIRK-bisubstrate inhibitor ternary complex are semi-transparent. Mg2+ ions and water molecules are represented as purple and red spheres, respectively. Hydrogen bonds and bonds to the Mg2+ ion are represented as dashed and solid black lines, respectively. Only the modified tyrosine from the peptide moiety (binary) complex and the cIRK-MgAMPPNP-peptide (ternary) complex15. Oxygen atoms are colored red, nitrogen atoms blue, sulfur atoms green, and phosphorus atoms yellow. Bonds/carbon atoms are colored orange for the binary complex and green for the ternary complex. Bonds and atoms of the t of the inhibitor is shown. 'BSI' indicates the bisubstrate inhibitor in the binary complex, 'Y(P0)' the substrate tyrosine in the ternary complex, and 'PNP' the ATP analog AMPPNP in the ternary complex. Selected secondary structural elements (aC and b3) are shown. Figure prepared with GRASP28, BOBSCRIPT29, and MOLSCRIPT30.

Figure 4:
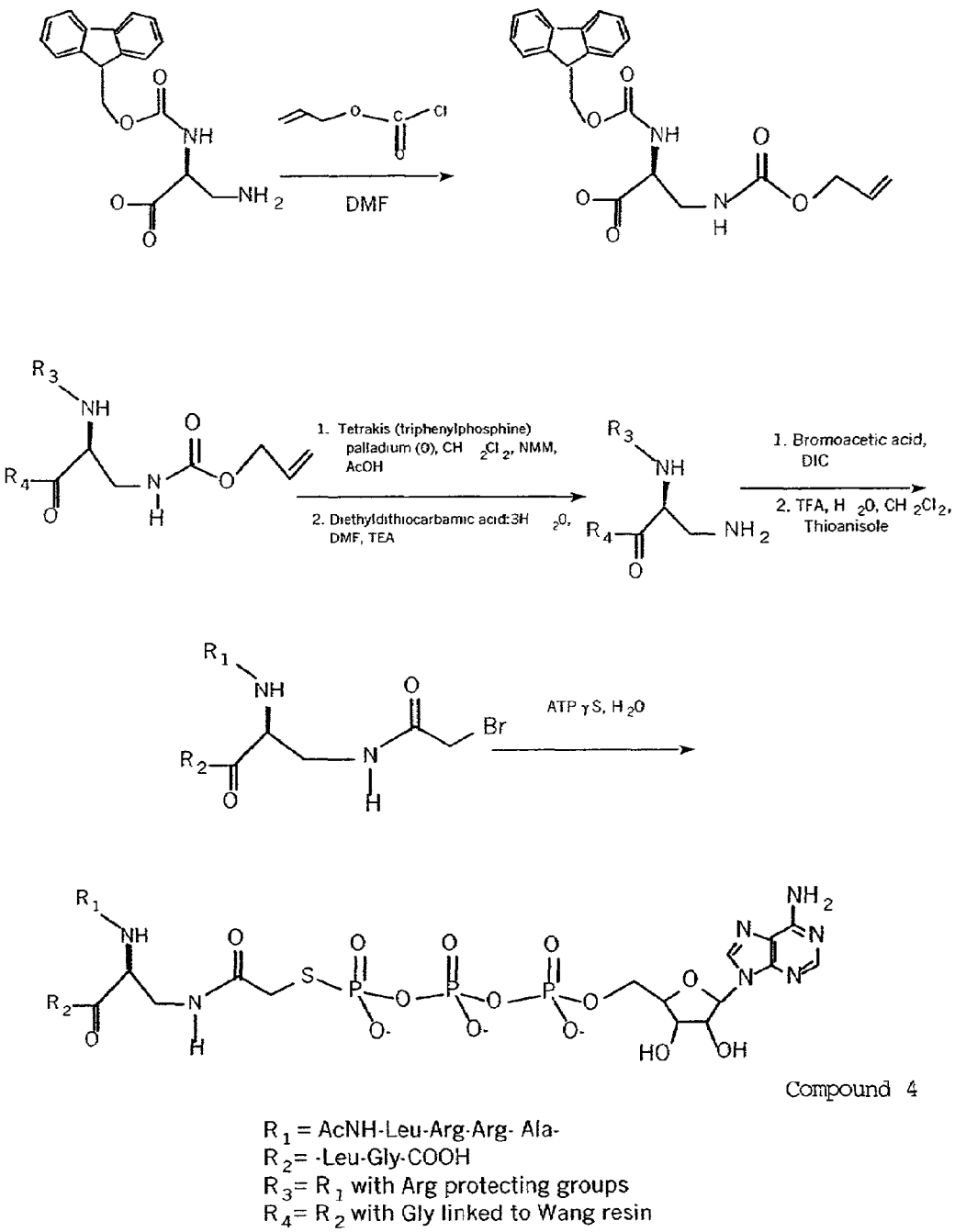

FIG. 4 shows the synthesis and structure of the kemptide.-ATP(S conjugate as an inhibitor of protein kinase A. $R_1$=AcNH-Leu-Arg-Arg-Ala- (SEQ ID NO: 6), $R_2$=-Leu-Gly-COOH, $R_3$=$R_1$ with Arg protecting groups; $R_4$=$R_2$ with Gly linked to Wang resin.

Figure 5:
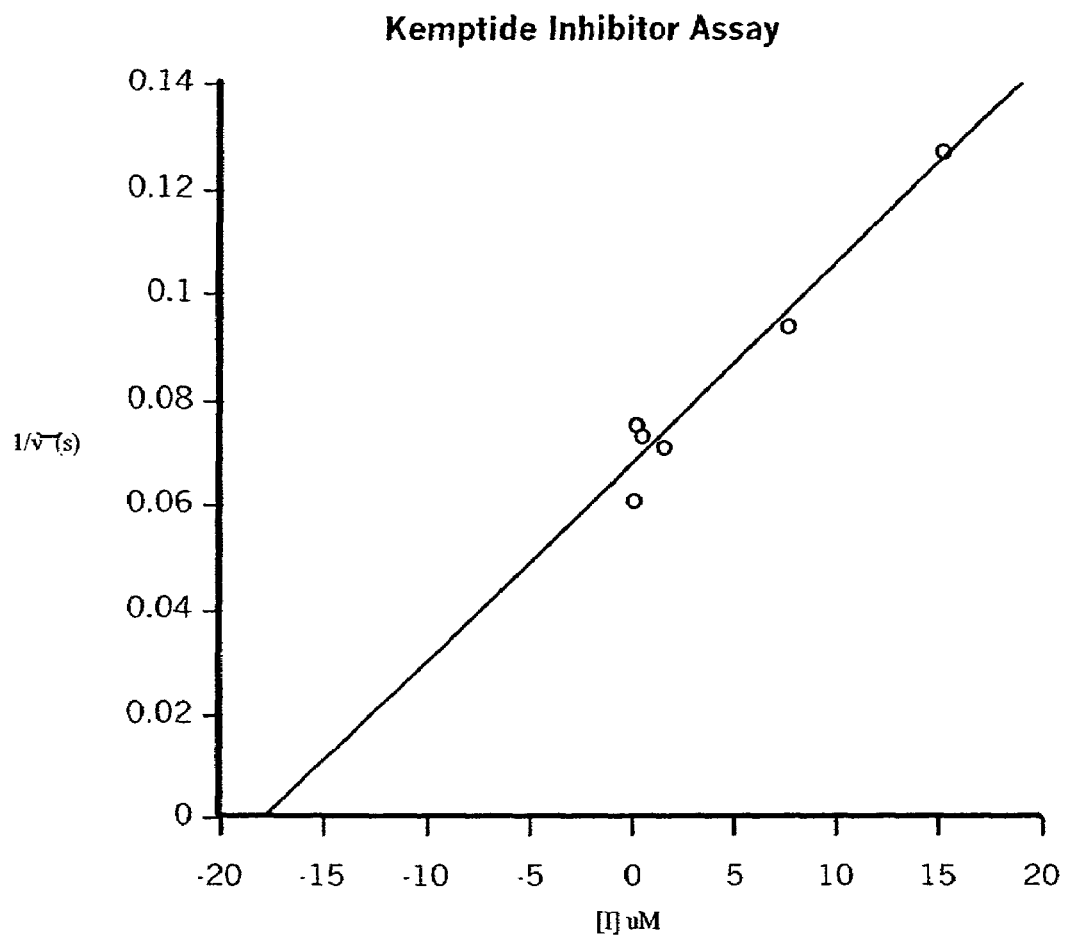

FIG. 5 shows a kinetic inhibition assay for protein kinase A.

Figure 6:
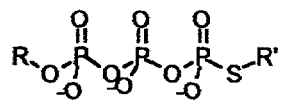
Figure 6:
Figure 6:
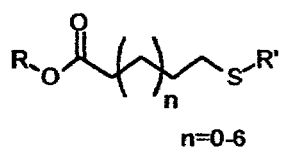
Figure 6:
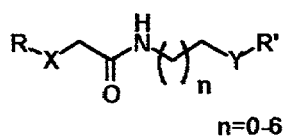
Figure 6:
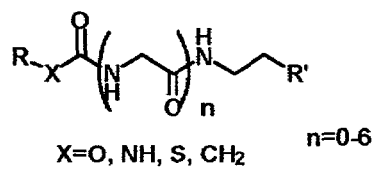
Figure 6:
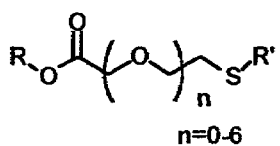

FIG. 6 shows substitutable groups for the triphosphates of ATP in a bisubstrate kinase inhibitor.

DETAILED DESCRIPTION OF THE INVENTION

It is a discovery of the present invention that design and manipulation of the dimensions of bisubstrate inhibitors of protein kinases can dramatically improve their inhibitory properties. In particular, the inventors have designed the distance between the two substrate-like moieties to mimic the dimensions of a dissociative transition state, i.e., a dimension of greater than 4.9 Å measured from a gamma phosphorus of the nucleotide or nucleotide analog moiety to the proton donor in the peptide moiety.

Bisubstrate inhibitors typically contain one moiety which is a nucleotide or nucleotide analog moiety, which mimics the natural substrate ATP. Suitable moieties include ATP, ATPγ-S, GTP, CTP, TTP, UTP, GTPγ-S, CTPγ-S, TTPγ-S, UTPγ-S, genistein, staurosporine, K252, quercetin. Analogs of nucleotides to which cells are more permeable are preferred. Analogs may, for example, have uncharged alkyl groups in place of one or more of the phosphate groups. Such alkyl groups may be $C_1$ to $C_6$ alkyl groups, including methyl, ethyl, butyl, pentyl, hexyl, and the branched chain isomers thereof. Preferably the alkyl groups will be $C_1$ to $C_3$. These groups may be optionally substituted by one or more halo, hydroxy, alkoxy, amino, or lower alkylamino groups. Examples of possible replacements for the phosphate groups of a nucleotide are shown in FIG. 6.

Bisubstrate inhibitors typically contain a second moiety which is a peptide having residues similar to that of the natural protein substrates of the particular protein kinase. Such peptides can be determined for each additional protein kinase by methods known in the art, including but not limited to library-based techniques[22,23]. One peptide useful for the insulin receptor kinase is known in the art and called irktide (Lys, Lys, Lys, Leu, Pro, Ala, Thr, Gly, Asp, Tyr, Met, Asn, Met, Ser, Pro, Val, Gly, Asp (SEQ ID NO:1)). A peptide useful for protein kinase A is known in the art and called kemptide (Leu, Arg, Arg, Ala, Ser, Leu, Gly (SEQ ID NO:2)). Peptides can be modified as described in more detail below. The peptide moieties of the bisubstrate inhibitors need not contain all of the amino acid residues identified above. Fewer may be required than the total. Thus as few as 4, 5, 6, or 7 of the amino acid residues may be sufficient to provide the requisite specificity. In addition, the residues may be modified to improve their access to cells. For example, membrane translocating sequences are known in the art and can be appended to the peptides of the bisubstrate inhibitors. One such sequence is AAVALLPAVLLALLAP (SEQ ID NO:5) See *J. Bio. Chem.* 270: 14255, 1995 and *Nature Biotech.* 16: 370, 1998. Such sequences can be advantageously placed at the N-terminal or C-terminal. A Human Immunodeficiency Virus TAT sequence can also be used to improve access to cells by the bisubstrate inhibitors. See Schwarze et al., *Science* 285:1569, 1999. One means of stabilizing the peptide sequence is to substitute carbon-carbon bonds in place of amide bonds. Other suitable replacements include that of NH with O (depsipeptide), use of urethane moieties to replace one or more amino acid residues, and the use of peptoids to replace amino acid residues. See *J. Med. Chem.* 37:2678 (1994) and *Angewandte Chemie Int'l Ed.* 34:907 (1995). Such peptides, peptoids, peptidomimetics are within the contemplation of the invention and are referred to herein as peptide moieties.

In order to make particular inhibitors with suitable tethers, the tyrosine residue of irktide is modified so that the phenolic oxygen is replaced with a nitrogen. Similarly, for the inhibitor of PKA, the serine residue is modified by substituting a nitrogen for the hydroxyl oxygen. Similarly, for threonine protein kinases, the hydroxyl oxygen can be replaced with a nitrogen. The tethers can comprise carbon, hydrogen, or oxygen atoms.

The bisubstrate inhibitor of insulin receptor kinase (IRK) can be used to inhibit the kinase in vitro and in vivo. In vitro it can be used to study mechanism. The inhibitor can be bound to the kinase and crystallized. The structure of the bound complex can be determined as is known in the art, e.g., by X-ray crystallography and/or NMR. The structure can be used to design still better inhibitors. In vivo it can be administered to achieve therapeutic ends. Thus it can be used to combat inflammation, cancer, cardiovascular disease, endocrine disorders, immune disorders, Alzheimer's disease, diabetes, and restenosis. The bisubstrate inhibitors can be administered by any means known in the art, including but not limited to intravenous, intramuscular, subcutaneous, intraperitoneal, and orally.

A bisubstrate inhibitor of protein kinase A (PKA) is also provided It too, contains a nucleotide or nucleotide analog moiety and a peptide moiety. The moieties are linked by a tether that comprises a proton donor. The tether is $\geq 4.9$ Å measured from a gamma phosphorus of the nucleotide or nucleotide analog to the proton donor. The PKA inhibitor differs from the IRK inhibitor in the peptide moiety. Not only is the nature of the peptide moiety different, presumably reflecting the kinases' different physiological substrates, but the linkage to the tether differs. In the case of the PKA inhibitor the hydroxyl oxygen of the serine residue is replaced with a nitrogen, forming a diaminopropionic acid residue.

Like the IRK inhibitor, the PKA inhibitor can be used to inhibit its enzyme target either in vitro or in vivo. Thus the compound can be contacted with the enzyme in a cell free system, suitable for kinetic studies, in cells in culture, and in whole animals, where therapeutic effects can be obtained. Other bisubstrate kinase inhibitors can be similarly used.

The present invention establishes a new approach to protein kinase inhibition based in part on mechanistic and structural considerations of a predicted dissociative transition state for these enzymes. This method is generalizable to other protein kinases based on the distinctive peptide substrate sequence selectivities of the individual enzymes. This permits design of inhibitors as biological and structural tools based on the peptide specificity of a protein kinase. Peptide specificity can be established by one of several library-based techniques[22, 23]. Whereas lead compounds may demonstrate suboptimal pharmacokinetic properties due to substituents which are peptides and nucleotides, such properties can be improved using phosphate surrogates and peptidomimetics as discussed above. Since different protein kinases may have overlapping peptide substrate selectivities, greater specificity for inhibition of individual kinases may also be achieved by synthetic refinements of the nucleotide and peptide moieties. By adding a new dimension of molecular recognition to the already high potency of nucleotide analog-based protein kinase inhibitors, these mechanism-based inhibitors constitute an entirely new class of therapeutically useful agents.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

Design of Inhibitor of IRK

Figure 1:
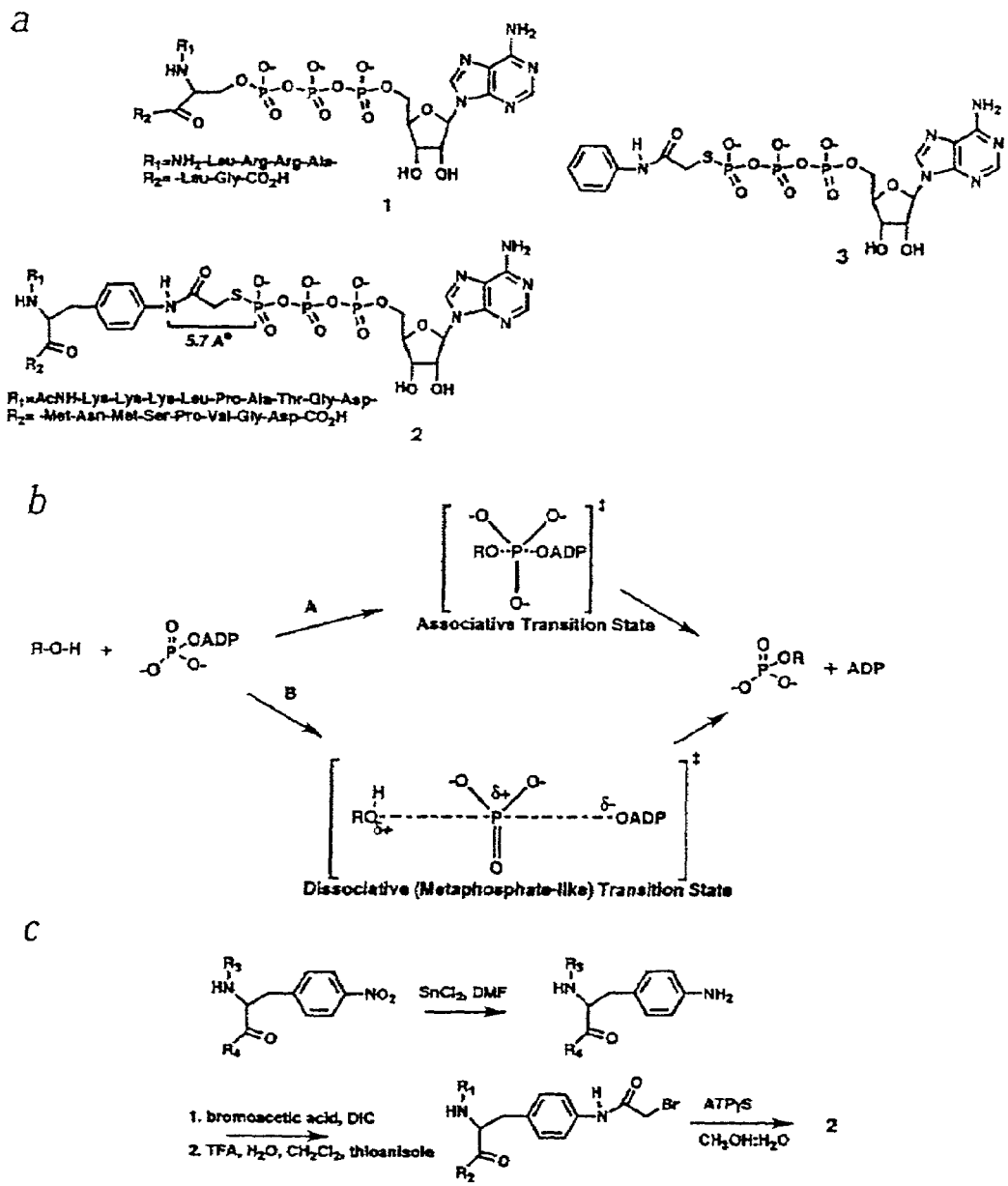
FIG. 1. Synthetic compounds and mechanistic schemes. a, Designed protein kinase bisubstrate analog inhibitors. Compound 1 was synthesized and studied by Gibson and colleagues[8] as a potential PKA inhibitor $R_1$ of Compound 1 is SEQ ID NO:6. Compound 2 was designed based on a dissociative transition state for phosphoryl transfer. Distance between the anilino nitrogen and the gamma-phosphorus was calculated using Chem3D assuming an extended conformation of the acetyl linker. The peptide sequence is derived from IRS72727. Compound 3 was prepared to evaluate the relative contribution of the peptide residues toward inhibition. b, Scheme illustrating associative vs dissociative transition states for phosphoryl transfer. ROH is the nucleophile (tyrosine phenol in this work) attacking the g-phosphoryl group of ATP, and ADP is the leaving group. Associative transition state (path A) in this work is defined as more than 50% bond formation between the nucleophilic oxygen and the phosphorus, which occurs with at least 50% leaving group residual bond formation present. Dissociative transition state (path B) in this work is defined as less than 50% bond formation between the nucleophile and the phosphorus, which occurs before the leaving group-phosphorus bond is at least 50% broken. c, Synthetic scheme toward the preparation of bisubstrate analog 2. R1=AcNH-Lys-Lys-Lys-Leu-Pro-Ala-Thr-Gly-Asp- (SEQ ID NO: 3); R2=-Met-Asn-Met-Ser-Pro-Val-Gly-Asp-CO2H (SEQ ID NO: 4); R3=R1 with side chain protected residues; R4=R2 with side chain protected residues and Asp linked to Wang resin.

Compound 1 has a Ser-O-to-P bond distance (1.7 Å) more compatible with a fully associative reaction mechanism for phosphoryl transfer by a protein serine kinase (FIG. 1b). In such a transition state a bond is largely formed between the attacking oxygen and the reactive γ-phosphorus atom, while the bond to the departing ADP would not yet have been significantly broken (FIG. 1b). In contrast, recent studies of two protein tyrosine kinases in which the nucleophilicity of the attacking tyrosyl's hydroxyl was varied have provided strong evidence for a dissociative or metaphosphate-like transition state[6, 12]. A dissociative transition state for phosphoryl transfer catalyzed by a protein kinase, analogous to an SN1 reaction in organic chemistry, is one in which the importance of nucleophilicity of the attacking hydroxyl is diminished and departure of the leaving group (ADP) is well advanced (FIG. 1b). Dissociative transition states are well-established for non-enzymatic phosphate monoester phosphoryl transfer reactions but have been considered more controversial for the corresponding enzyme-catalyzed reactions[13, 14]. A prediction for such a fully dissociative transition state is that the 'reaction coordinate distance' between the entering nucleophilic oxygen and the attacked phosphorus should be $\geq 4.9$ Å. This is based on the assumptions that the g-phosphoryl group moves toward the entering oxygen and that this nucleophile and the ADP are fixed, probably as they appear in the ground-state ternary complex that precedes the transition state[14].

For a transition state with greater associative character, the reaction coordinate distance could be $\geq 3.3$ Å, indicating compression[14]. High resolution X-ray and NMR structures of various protein kinase complexes with nucleotide and peptide substrate analogs have yielded conflicting values for such distances[14-16], however these studies by necessity have employed unreactive substrate analogs which could affect the outcomes.

In reconsidering the design of a bisubstrate analog based on the above parameters of (largely) dissociative reaction mechanisms for protein kinases, we hypothesized that a peptide-ATP bisubstrate analog 2 in which the distance between the tyrosine nucleophilic atom and the g-phosphorus was set to approximately 5 Å (5.66 Å in extended form;

FIG. 1a) by a short linker might show more potent inhibition toward a protein tyrosine kinase than 1 showed toward PKA. A second design feature was based on the fact that proton removal from the tyrosine's hydroxyl occurs late in the dissociative reaction mechanism,[6, 12] and that the phenolic hydroxyl serves as a hydrogen bond donor to the conserved catalytic aspartate (Asp 1132 of the insulin receptor). To exploit this interaction, the tyrosine oxygen was replaced with a nitrogen atom which could serve as a hydrogen bond donor while simultaneously being incorporated into a tether. Our choice of target enzyme for the inhibitor was the insulin receptor protein tyrosine kinase (IRK) because: 1) efficient peptide substrates (including IRS727) for this enzyme have been well characterized kinetically[6]; 2) solution phase studies have provided direct evidence for a dissociative transition state for this enzyme[6]; 3) a high resolution crystal structure of this enzyme in a ternary complex with peptide substrate and an ATP analog has been determined[15]; and 4) no potent inhibitors have been reported for this important signalling enzyme or for the highly related insulin-like growth factor receptor protein tyrosine kinase.

Example 2

Synthesis and Kinetic Analysis of a Bisubstrate Inhibitor

Synthesis of compound 2 was carried out as shown in FIG. 1c. The protected peptide was assembled using solid-phase peptide synthesis using Fmoc chemistry, in which the single tyrosine of IRS727 was replaced with commercially available nitrophenylalanine. The nitro group was reduced with SnCl2 and the aniline function was bromoacetylated via standard coupling conditions. The peptide was cleaved from the resin and deblocked with trifluoroacetic acid, water, and thioanisole and purified by reversed phase HPLC. The bromoacetylated peptide was reacted with ATPγS in aqueous solution at pH 7, which resulted in chemoselective displacement of the bromide by the phosphorothioate. The peptide-ATP conjugate 2 was purified by reversed phase HPLC and characterized by electrospray mass spectrometry and 1H NMR. While it was stable in aqueous solution at neutral pH and room temperature for >12 h, it was unstable in acidic solution (pH 2), decomposing with a half life of ~2 hours. It could be stored in frozen solution at −80° C. for several weeks without detectable decomposition.

Methods

Synthesis of Compounds 2 and 3

The nitrophenylalanine peptide starting material (FIG. 1c) was assembled on Wang resin using automated solid phase peptide synthesis via the Fmoc strategy (0.3 mmol scale). While still in the solid phase, the nitro group was reduced with $SnCl_2 \cdot 2H_2O$ (6 mmol) in dimethylformamide for 24 h at room temperature with gentle stirring. It was washed with dimethylformamide and $CH_2Cl_2$ and dried. The resin was then treated with bromoacetic acid (2.5 mmol), diisopropylcarbodiimide (2.5 mmol) in dimethylformamide for 5 h at room temperature with gentle mixing. The resin was washed and dried as above prior to treatment with cleavage and deblocking conditions (5 mL trifluoroacetic acid, 1.5 mL $CH_2Cl_2$, 0.25 mL $H_2O$, 0.1 mL thioanisole) for 30 min at room temperature. The particulate was removed by filtration through scintered glass and the filtrate was concentrated and treated with cold ether to precipitate the bromoacetylated peptide. The crude bromoacetylated peptide was washed once more with cold ether, dried under vacuum, and purified by preparative reversed phase HPLC (gradient with $H_2O$: $CH_3CN$: 0.05% $CF_3CO_2H$, UV monitored at 214 nm) to yield 71 mg of pure material, and electrospray mass spectrometry was used to confirm its structural identity. The purified bromoacetylated peptide (17 mg) was dissolved in 4:1 $MeOH$:$H_2O$ (3.6 mL) and treated with ATP γS (adenosine 5'-O-3-thiotriphosphate, Boehringer, 0.02 mmol) for 24 h at room temperature. The conjugate 2 was subsequently purified by reversed phase HPLC (gradient with $H_2O$: $CH_3CN$, neutral pH, UV monitored at 214 or 260 nm) and lyophilized to yield 12 mg. Electrospray mass (negative ion) and 1H NMR spectra confirmed the correctness of the assigned structure. The concentration of 2 in aqueous solution was determined by amino acid analysis (Harvard Univ. Microchemistry Facility). The compound was stored at pH 7 in aqueous solution at −80° C. and periodically monitored for decomposition by HPLC.

Synthesis of 3 was carried out by reacting bromoacetanilide and ATP-γS analogously to the production of 2. The product 3 was purified by reversed phase HPLC and the pure product characterized by 1H NMR, electrospray mass spectrometry and quantified by UV.

Example 3

Kinetics of Inhibition

Figure 2:
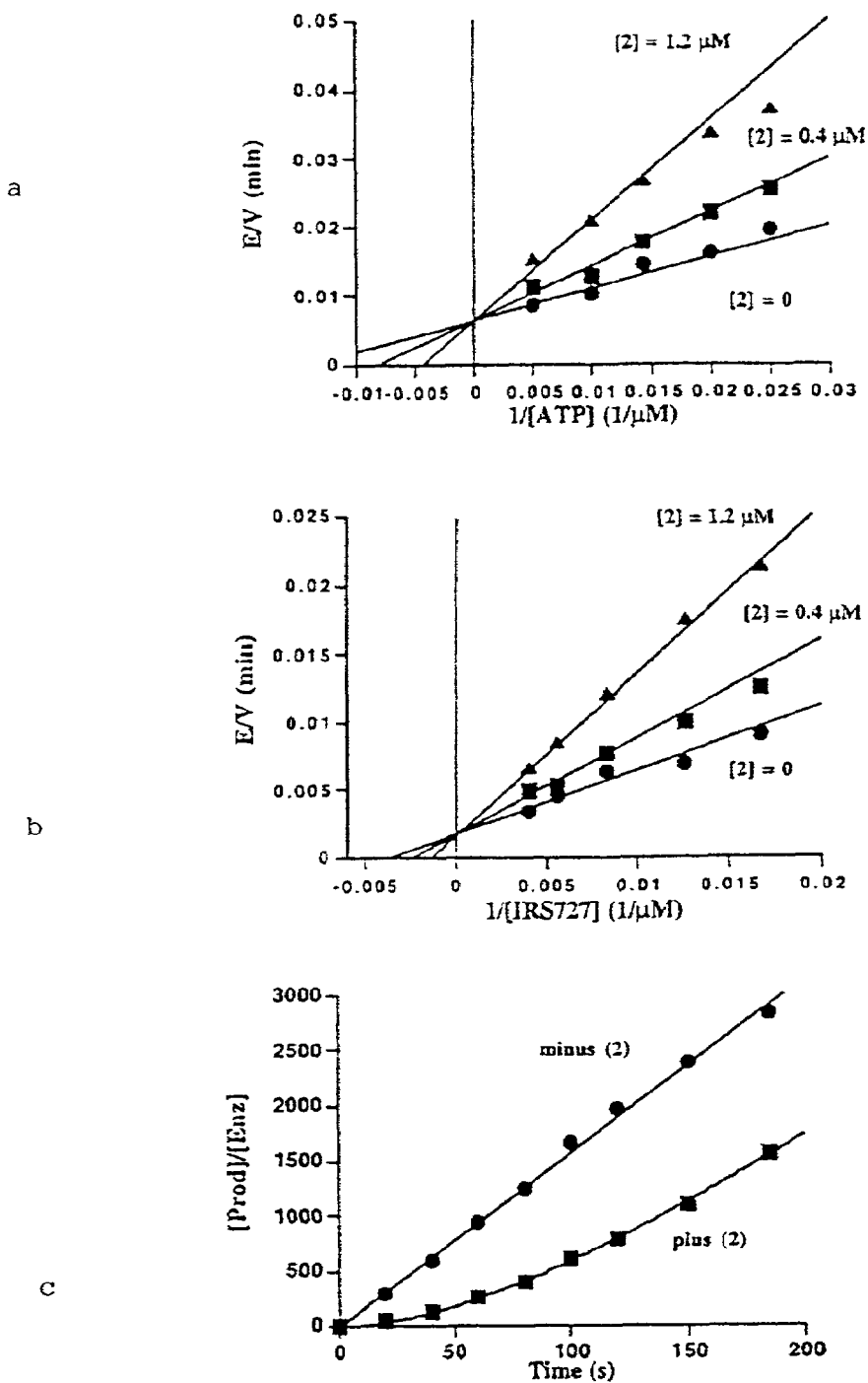
FIG. 2. Kinetic analysis of the inhibition of IRK by Bisubstrate Analog 2. Assays were carried out using activated recombinant IRK as described previously. 6 a, E/V vs. 1/ATP in the presence of varying [2]. Conditions: fixed IRS727 concentration (120 mM), 20 mM MgCl2, 0.5 mM DTT, 6 nM IRK, 0.05% bovine serum albumin, Tris-Acetate pH 7, 10 min reaction time. b, E/V vs. 1/IRS727 in the presence of varying [2]. Conditions same as for a except fixed ATP (80 mM), 8 nM IRK and 5 min reaction time. Duplicate measurements agreed within ±15%. Data for a and b were globally fit to the equation for linear competitive inhibition.

Kinase assays with compound 2 revealed it to be a potent inhibitor of IRK (FIG. 2). Using a steady-state kinetic analysis, compound 2 was a linear competitive inhibitor versus both nucleotide (FIG. 2a) and peptide (FIG. 2b) substrates with a $K_i$ of 370 nM (extrapolated to zero substrates), which is 190–760 fold lower than the $K_m$'s of the substrates ($K_{m\ app}$ (ATP)=71 μM; $K_{m\ app}$ (IRS727)=280 μM). In an alternative analysis of 2, the $IC_{50}$~10 μM at a concentration of 1 mM ATP and 0.3 mM IRS727. By using a rapid dilution analysis, the $k_{off}$ was measured to be 0.013 $s^{-1}$ (FIG. 2c), which is also consistent with its tight-binding behavior. The calculated second order rate constant $k_{on}$ for 2 binding to IRK is $3.5 \times 10^4$ $M^{-1}s^{-1}$ which is substantially slower than a predicted diffusional encounter rate ($10^8$–$10^9$ $M^{-1}s^{-1}$) and suggests that a "slow" conformational change may be responsible for reaching the tightly bound complex[17]. Compound 2 represents the most potent inhibitor yet reported for IRK. The potency of 2 compares favorably to bisubstrate analog inhibitors designed for other (non-protein kinase) enzymes[9]. The most potent bisubstrate analog inhibitors can show binding free energies equal to the sum of the binding energies of the two substrates. The binding energy of compound 2 (8.9 kcal/mol) is approximately equal to the sum of its two parts (4.1 kcal/mol for IRS727 peptide binding and 5.1 kcal/mol for ATPγS binding,) confirming that each substrate-like part of compound 2 contributes to the binding affinity.

To further probe the basis of the potency of 2, the derivatized ATP analog 3 lacking the polypeptide portion of compound 2 was prepared and tested as an IRK inhibitor. It was a linear competitive inhibitor of IRK versus ATP with a $K_i$ of 114 μM. This is only 2-fold tighter binding than ATP-γS alone ($K_i$ of 210 μM) and approximately 300-fold weaker as an inhibitor than 2, indicating that the peptide moiety is an essential contributor to the inhibitory potency of 2 and that the anilino-tethering group present in 3 accomplishes little by itself.

An additional inhibitor was formed like compound 2 but containing only two phosphate groups on the nucleotide moiety. It was less than 100-fold as inhibitory as compound 2. This confirms the criticality of the tether distance of greater than 4.9 Å.

The specificity of inhibition was also tested by assaying 2 as an inhibitor of the protein tyrosine kinase Csk18. The peptide binding selectivity for Csk is quite different from IRK, and the IRS727 peptide moiety would be predicted to bind poorly to this enzyme[19]. As anticipated 2 was only a modest inhibitor of Csk with an approximate $K_i$=40 μM ($K_m$ (ATP) of 195 μM). Thus the bisubstrate analog approach should allow for kinase selectivity based in part on peptide sequence.

Kinetic Analysis of IRK Inhibition by Compound 2

Assays were carried out using activated recombinant IRK as described previously[6]. For E/V vs. 1/ATP plot the conditions were: 120 mM IRS727 concentration, 20 mM $MgCl_2$, 0.5 mM DTT, 6 nM IRK, 0.05% bovine serum albumin, 50 mM Tris-Acetate pH 7, 10 min reaction time. For E/V vs. 1/IRS727 in the conditions were the same except fixed ATP (80 mM) was employed, 8 nM IRK and 5 min reaction time. Duplicate measurements agreed within ±15%. Data for these plots were globally fit to the equation for linear competitive inhibition:

$v=V_m(S)/[K_m(1+I/K_i)+S]$; v=initial velocity, $V_m$=maximal velocity, S=substrate concentration, $K_m$=Michaelis constant. Inclusion of a $K_i$-intercept term (for a mixed competitive inhibition calculation) for either analysis did not reduce standard errors in the global fit and led to very high standard errors for the $K_i$-intercept terms, thereby adding confidence to our selection of the linear competitive inhibition model for these plots.

For the $k_{off}$ measurement of compound 2 from IRK, the conditions: Incubation of 1 mM IRK +/−5 mM 2 for 10 min in reaction buffer (20 mM $MgCl_2$, 0.5 mM DTT, 0.05% BSA, 50 mM Tris-Acetate, pH 7) then dilute 1:50 into reaction buffer containing 1 mM ATP and 250 mM peptide[6] IRS939 and measure conversion by HPLC at times shown. To determine $k_{off}$, data were fit to the equation[17]:

$P=vs*(t-[1-e-k_{off}t])k_{off}$; P=Product concentration, vs=steady-state velocity, t=time and koff is the first-order rate constant for dissociation of 2 from the enzyme. koff=0.013±0.001$s_{-1}$.

Example 4

Crystal Structure of Compound 2 Bound to the Insulin Receptor Kinase

To understand the structural details of IRK inhibition by 2, we determined the crystal structure of 2 bound to the core tyrosine domain of the insulin receptor (cIRK) at 2.7 Å resolution (Table 1 and FIG. 3). cIRK was autophosphorylated in vitro to yield the tris-phosphorylated, activated form of cIRK in which Tyr 1158, Tyr 1162, and Tyr 1163 in the activation loop are phosphorylated. The bisubstrate inhibitor was co-crystallized with cIRK, producing trigonal crystals with the same unit cell dimensions as crystals of the ternary complex (cIRK/IRS727/MgAMPPNP)15. The inhibitor-cIRK structure is very similar to the structure of the ternary complex, with an overall root-mean-square deviation of only 0.22 Å for 303 Ca atoms of cIRK.

TABLE 1

X-ray data collection and refinement statistics

| Data collection | |
|---|---|
| Resolution (Å) | 30.0–2.7 |
| Observations | 42217 |
| Unique reflections | 9633 |
| Completeness (%) | 96.5(91.9)1 |
| $R_{sym}$ 2(%) | 11.4(33.9)1 |
| Refinement | |
| Number of atoms | |
| Protein | 2370 |
| Inhibitor | 125 |
| Water | 23 |
| Mg2+ | 2 |
| Resolution (Å) | 30.0–2.7 |
| Reflections | 9342 |
| $R_{cryst}$3/$R_{free}$ (%) | 21.4/27.0 |
| R.m.s. deviations | |
| Bond lengths (Å) | 0.007 |
| Bond angles (°) | 1.5 |
| B-factors4 (Å2) | 1.3 |
| Average B-factors (Å2) | |
| All atoms | 20.6 |
| Protein | 20.1 |
| Inhibitor (ATPγ S + linker) | 15.4 |
| Inhibitor (peptide) | 34.2 |

1Overall (30.0–2.7Å) value given first, followed by value (in parentheses) in the highest resolution shell (2.8–2.7Å).
2$R_{sym}$ = 100 × Σ|I-<I>|/ΣI.
3$R_{cryst}$ = 100 × Σ||Fo|-|Fc||/Σ|Fo|, where Fo and Fc are the observed and calculated structure factors, respectively (Fo>Oσ). $R_{free}$ determined from 5% of the data.
4For bonded protein atoms.

Several remarkable features were observed in the active site of cIRK. First, two mechanism-based design components were validated: 1) the distance between the γ-phosphorus and the anilino nitrogen atom (corresponding to the phenolic oxygen of tyrosine) was 5.0 Å, the expected reaction coordinate length for a dissociative mechanism as discussed above; 2) a 3.2 Å hydrogen bond between the anilino nitrogen and the key catalytic aspartate (Asp 1132) was evident. Serendipitously, the carbonyl oxygen of the linker is coordinated to a Mg2+ ion (O—Mg=2.2 Å), replacing a water molecule at that position in the ternary complex (FIG. 3c) and preserving the octahedral coordination of this Mg2+ ion. A second Mg2+ ion appears to have a lower occupancy in the binary complex than was observed in the ternary complex. In the binary complex, the side chain of invariant Lys 1030 is hydrogen-bonded to invariant Glu 1047 as well as to the a-phosphate group. This is in contrast to the ternary complex in which a hydrogen bond from Lys 1030 to the a-phosphate group was observed, but the Lys 1030-Glu 1047 distance was 4.4 Å. A salt bridge between the invariant lysine and glutamate may be required for efficient phosphoryl transfer 20.

The peptide moiety of the bisubstrate inhibitor binds to cIRK in a similar manner to that observed in the ternary complex15: an anti-parallel b-strand interaction is present between residues P+1–P+3 of the peptide and Gly 1169-Leu 1171 of the activation loop, and the P+1 and P+3 methionines are positioned in shallow hydrophobic pockets on the surface of the C-terminal kinase lobe. Several IRS727 residues that had been disordered in the ternary complex, P-3 to P-5 and P+4 to P+7, are visible in the complex with the bisubstrate inhibitor (same unit cell), suggesting a more stable interaction (FIG. 3b). The peptide portion of the bisubstrate inhibitor outside of the core recognition region (P−1 to P+3) follows a unique path (FIG. 3a). Interestingly, the residues N-terminal to the modified tyrosine do not lie along the extended peptide binding groove defined largely by residues in a-helix D, as observed for PKI bound to PKA21; the P−5 proline of the bisubstrate inhibitor is adjacent to Gly 1005 of the nucleotide-binding loop in the N-terminal lobe. This may be due to charge repulsion between the three N-terminal lysines of the peptide moiety and Arg 1089 and Arg 1092 of cIRK, which are exposed on a-helix D. In addition, residues at the C-terminus of the peptide moiety (P+4, etc.) lie in a shallow groove bounded by the activation loop and a-helices EF and G. This latter interaction was unanticipated and could possibly be associated with slow release of the peptide.

Crystal Structure of cIRK with Compound 2

Tris-phosphorylated cIRK (residues 978–1283) was prepared as described[15]. Crystals were grown at 4° C. by vapor diffusion in hanging drops containing 1.0 μL of protein solution (280 mM cIRK (10 mg/mL), 400 μM of the bisubstrate inhibitor, and 1.2 mM MgCl2) and 1.0 μL of reservoir buffer (18% polyethylene glycol 8000, 100 mM Tris-HCl, pH 7.5). Crystals belong to space group P3221 with unit cell dimensions a=b=66.3 Å, c=138.1 Å. Crystals were transferred into a cryosolvent consisting of 30% polyethylene glycol 8000, 100 mM Tris-HCl, pH 7.5, and 15% ethylene glycol. A data set was collected from a flash-cooled crystal on a Rigaku RU-200 rotating anode equipped with a Rigaku R-AXIS IIC image plate detector. Data were processed using DENZO and SCALEPACK24. Rigid-body, simulated annealing, positional and B-factor refinement were performed with CNS25 and model building with O26. Bulk solvent and anisotropic B-factor corrections were applied.

Example 5

Synthesis of Kemptide-ATPγS Conjugate as Inhibitor of PKA

An n-Alloc protecting group was added to the side chain amine of the commercially available diaminopropionic acid (DAP) residue by reacting DAP (500 mg: 1.5 mmol) with allyl chloroformate (163 uL: 1.5 mmol) in dimethylformamide (DMF) at room temperature for 24 hours. The protected residue was purified using silica gel size exclusion column chromatography (gradient elution MeOH: $CH_2Cl_2$). The eluting fractions were monitored using thin layer chromatography, mass spectrometry and NMR. The fractions containing DAP(n-alloc) were combined, dried under vacuum and used to synthesize the DAP(n-alloc) kemptide peptide. The DAP(n-alloc) kemptide peptide (FIG. 4) was prepared on a solid phase Wang resin (0.1 mmol scale) using Fmoc chemistry. The DAP(n-alloc) kemptide peptide was treated while on the solid phase with 70% $CH_2Cl_2$, 15% N-methyl morpholine, 15% acetic acid solution (5 mL) into which 450 mg tetrakis(triphenylphosphine) palladium (0) was added. This deprotection reaction was done under argon at room temperature for two hours with gentle shaking. The reaction solution was removed using a Poly Prep® chromatography filter column (BioRad) and the resin was washed with $CH_2Cl_2$ (50 mL) before rinsing with a palladium chelating solution consisting of 20 mL DMF, 225 mg diethyldithiocarbamic acid:$3H_2O$ and 250 uL triethylamine (TEA). The resin was washed with 5%(v/v) TEA in DMF (50 mL) then methanol (50 mL) and dried. Bromoacetic acid (342 mg) was dissolved in a solution of DMF (5 mL) and diisopropylcarbodiimide (0.4 mL), added to the dried resin and allowed to react with the peptide for 5 hours at room temperature with gentle shaking. The resin was filtered and washed as described above, dried and then treated with a cleavage/deprotection solution (5 mL trifluoroacetic acid, 1.5 mL $CH_2Cl_2$, 250 (L dd$H_2O$, 100 (L thioanisole) for 1 hr at room temperature. The released peptide was filtered from the resin, vacuum concentrated and then precipitated using cold ether (25 mL). The precipitate was dried under vacuum, dissolved in 7 mL of water and purified using reverse-phase preparative HPLC (gradient elution: $H_2O$:$CH_3CN$:0.05% trifluoroacetic acid (v/v), UV analysis at 214 nm) to give 7.9 mg of bromoacetylated peptide. The bromoacetylated product was dissolved in $H_2O$ (2 mL) and reacted with ATPγS (20 nmol) with stirring for 24 hours at room temperature. The kemptide-ATPγS conjugate was purified from the reaction mixture using reverse phase preparative HPLC (gradient elution: $H_2O$, $CH_3CN$) and dried under vacuum to produce a final yield of 7 mg kemptide-ATPγS conjugate. The composition of the conjugate was confirmed using electrospray mass spectrometry and NMR data supported the proposed inhibitor structure. Concentration was determined using UV absorption at 260 nm.

Example 6

Inhibition of PKA using Kemptide-ATPγS Conjugate

Preliminary assays using the kemptide-ATPγS conjugate as a specific inhibitor of protein kinase A (PKA) have been performed and show the conjugate to be inhibitory to PKA. Reagents from Calbiochem's Protein Kinase A kit were used to perform the inhibition assays and recombinant mouse PKA (catalytic subunit) was also purchased from Calbiochem (enzyme concentration was established by Bradford analysis). A 0.76 mM stock solution of kemptide-ATPγS conjugate was prepared and used to make serial dilutions into an aqueous $MgCl_2$ solution (53 mM), producing a range of inhibitor concentrations from 144 uM to 1.4 μM with Mg2+ concentration of 47.7 mM. These were further diluted into water to produce a range of inhibitor solutions between 51 μM and 507 nM. An 11.25 μL aliquot from each of these solutions was pre-incubated with 7.5 μL of a 1.75 nM PKA enzyme solution (750 ug/uL bovine serum albumin) for 10 minutes at 30° C. after which 12.5 μL of pre-incubation mix was added to 12.5 μL of reaction mix (30 μM cold ATP, 50 μM biotinylated kemptide substrate, 0.04 uCi/μL γP-32 ATP, 80 mM Tris-HCl, 10 mM $MgCl_2$, pH 7.5) to initiate the enzymatic reaction. Reactions were quenched after 2 minutes with 10 μL 8.0 M guanidine HCl (8.0 M solution as reported by Calbiochem kit, however guanidine limit of solubility=6 M), treated with avidin solution, then run through a centrifugation column to which the avidin-bound phosphokemptide would adhere. The columns were placed in scintillation vials and radioactivity was measured using a scintillation counter. Dixon plot analysis of the resultant inhibition data is shown in FIG. 5. The calculated $K_i$ value versus ATP for this conjugate (assuming a reversible competitive inhibition model) is shown to be 9.56 μM. If the $K_i$ calculation is adjusted to account for zero substrate the $K_i$ value decreases to 4.6 μM.

Bisubstrate analog inhibitors such as the conjugate above have generated considerable interest because of their potential to be highly selective inhibitors for their specific enzyme targets[31]. These compounds, designed to bind enzymes that form a ternary complex in the transition state, gain specificity by linking moieties derived from the target enzyme's natural substrates. One of the challenges inherent in bisubstrate analog inhibitor design is the requirement that the molecule effectively mimic what the enzyme would normally see in its transition state active site. This potential limitation is greatly reduced by having structural information about the target enzyme's active site as well as an understanding of the chemical reaction mechanism used by the enzyme. Structural and mechanistic data supporting a dissociative mechanism of phosphoryl transfer for the insulin receptor kinase was used to design a potent bisubstrate analog inhibitor against this enzyme ($K_i$=370 nM, extrapolated to zero substrate)[32]. The kemptide-ATPγS conjugate described above was designed based on the structural homology of PKA's active site to the active site of the insulin receptor kinase as well as mechanistic data implicating a dissociative chemical mechanism for PKA. The bisubstrate analog inhibitor approach has been previously attempted for PKA. A conjugate featuring an ATP moiety directly linked to the kemptide serine was shown to be a weak inhibitor of PKA ($K_i$=226 μM versus ATP)[33]. The increased inhibition generated by our kemptide-ATPγS conjugate ($K_i$=9.6 μM versus ATP) may be a result of improved electronic and steric design, thus creating a molecule that more accurately reflects the true reaction intermediate. Continued optimization of linker distances, electronic interactions and peptide composition hold the potential to generate a highly specific and even more potent inhibitor for PKA.

REFERENCES

1) Hunter, T., Cell 100, 113–127 (2000).
2) Showalter, H. D. & Kraker, A. J. Pharmacol. Ther. 76, 55–71 (1997).
3) Lawrence, D. S. & Niu, J. Pharmacol. Ther. 77, 81–114 (1998).
4) G. Rosse, G. et al. Helvetica Chimica Acta 80, 653–670 (1997).
5) Yuan, C. J., Jakes, S., Elliott, S. & Graves, D. J. Biol. Chem. 265, 16205–16209 (1990).
6) Ablooglu, A. J. et al. J. Biol. Chem. 275, 30394–30398 (2000).
7) Cushman, M. et al. Int. J. Pept. Protein Res. 36, 538–543 (1990).
8) Medzihradszky, D., Chen., S. L., Kenyon, G. L. & Gibson, B. W. J. Am. Chem. Soc. 116, 9413–16209 (1994).
9) Silverman, R. B., The Organic Chemistry of Drug Design and Drug Action'(Academic, NY, 1992).
10) Ho, M., Bramson, H. N., Hansen, D. E., Knowles, J. R. & Kaiser, E. T. J. Am. Chem. Soc. 110, 2680–2681 (1988).
11) Uri, A., Raidaru, G., Jarv, J. & Pia, E. Bioorg. Med. Chem. Lett. 9, 1447–1452 (1999).
12) Kim, K. & Cole, P. A. J. Am. Chem. Soc. 120, 6851–6858 (1998).
13) Admiraal, S. J. & Herschlag, D. J. Am. Chem. Soc. 122, 2145–2148 (2000).
14) Mildvan, A. S. Proteins: Structure, Function, and Genetics 29, 401–416 (1997).
15) Hubbard, S. R. EMBO J. 16, 5572–5581 (1997).
16) Brown, N. R., Noble, M. E. M., Endicott, J. A. & Johnson, L. N. Nature Cell Biol. 1, 438–443 (1999).
17) Morrison, J. F. & Walsh, C. T. Adv. Enzymol. 61, 201–301 (1988).
18) Grace, M. R., Walsh, C. T. & Cole, P. A. Biochemistry 36, 1874–1881 (1997).
19) Sondhi, D., Xu, W., Songyang, Z., Eck, M. J. & Cole, P. A. Biochemistry 37, 165–172 (1998).
20) Taylor, S. S. & Radzio-Andzelm, E. Structure 2, 345–355 (1994).
21) Knighton, D. R. et al. Science 253 414–420 (1991).
22) Songyang, Z. et al., Nature 373, 536–539 (1995).
23) Till, J. H., Annan, R. S., Carr, S. A. & Miller, W. T. J. Biol. Chem. 269, 7423–7428 (1994).
24) Otwinowski, Z. & Minor, W. Methods Enzymol. 276, 307–326 (1997).
25) Brünger, A. et al., Acta Crystallogr. D54, 905–921 (1998).
26) Jones, T. A. Methods Enzymol. 115, 157–171 (1985).
27) Shoelson, S. E., Chatterjee, S., Chandhuri, M. & White, M. F. Proc. Natl. Acad. Sci. USA 89, 2027–2031 (1992).
28) Nicholls, A., Sharp, K. A. & Honig, B. Proteins 11, 281–296 (1991).
29) Esnouf, R. M. J. Mol. Graph. 15, 132–134 (1997).
30) Kraulis, P. J. J. Appl. Crystallogr. 24, 946–950 (1991).
31) Silverman, R. B. *The organic chemistry of drug design and drug action* (Academic Press, New York; 1992)
32) Parang, K., Till, J. H., Ablooglu, A. J., Kohanski, R. A., Hubbard, S. R., Cole, P. A. *Nature Structural Biology* 8, 37–41 (2001).
33) Medzihradszky, D., Chen, S. L., Kenyon, G. L., Gibson, B. W. *J. Am. Chem. Soc.* 116 9413–9419 (1994).

We Claim:
1. A bisubstrate inhibitor of insulin receptor kinase, wherein the bisubstrate inhibitor of insulin receptor kinase is Compound 2:
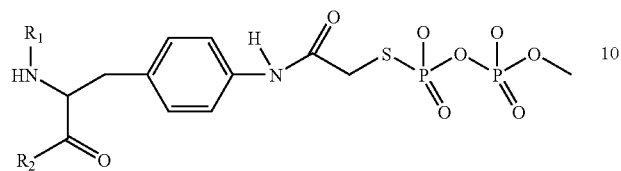
-continued
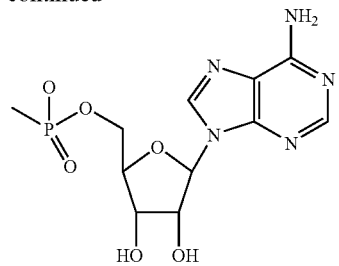
R₁ = AcNH—Lys-Lys-Lys-Leu-Pro-Ala-Thr-Gly-Asp (SEQ ID NO:3)
R₂ = Met-Asn-Met-Ser-Pro-Val-Gly-Asp—CO₂H (SEQ ID NO:4).
* * * * *

UNITED STATES PATENT AND TRADEMARK OFFICE
CERTIFICATE OF CORRECTION

PATENT NO. : 7,045,617 B2  Page 1 of 1
APPLICATION NO. : 09/811870
DATED : May 16, 2006
INVENTOR(S) : Philip A. Cole et al.

It is certified that error appears in the above-identified patent and that said Letters Patent is hereby corrected as shown below:

On Title Page
On the Cover Page, Title item (54):
  Please replace "BISBUBSTRATE" with --BISUBSTRATE--

Columns 17-18, Claim 1:
  Please replace the formula as it appears below:

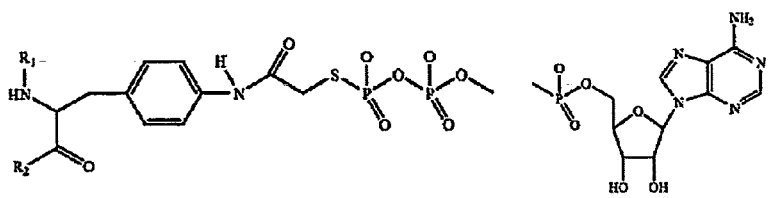

with the formula shown below (with three oxygen molecules having a negative charge):

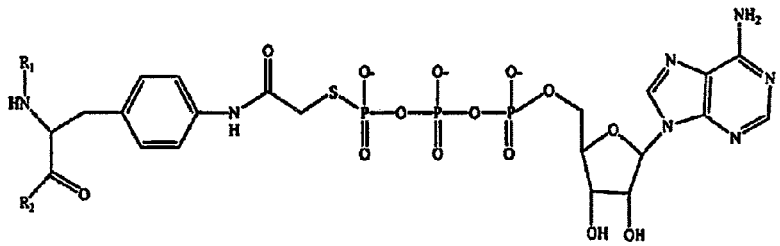

Signed and Sealed this

Twenty-eighth Day of November, 2006

JON W. DUDAS
*Director of the United States Patent and Trademark Office*

SEQUENCE LISTING

<160> NUMBER OF SEQ ID NOS: 6

<210> SEQ ID NO 1
<211> LENGTH: 18
<212> TYPE: PRT
<213> ORGANISM: Artificial Sequence
<220> FEATURE:
<223> OTHER INFORMATION: kinase substrates

<400> SEQUENCE: 1

Lys Lys Lys Leu Pro Ala Thr Gly Asp Tyr Met Asn Met Ser Pro Val
1               5                   10                  15

Gly Asp

<210> SEQ ID NO 2
<211> LENGTH: 7
<212> TYPE: PRT
<213> ORGANISM: Artificial Sequence
<220> FEATURE:
<223> OTHER INFORMATION: kinase substrates
<220> FEATURE:
<221> NAME/KEY: VARIANT
<222> LOCATION: (5)...(5)
<223> OTHER INFORMATION: serine may be modified to diaminopropionic acid

<400> SEQUENCE: 2

Leu Arg Arg Ala Ser Leu Gly
 1               5

<210> SEQ ID NO 3
<211> LENGTH: 9
<212> TYPE: PRT
<213> ORGANISM: Artificial Sequence
<220> FEATURE:
<223> OTHER INFORMATION: kinase substrates

<400> SEQUENCE: 3

Lys Lys Lys Leu Pro Ala Thr Gly Asp
 1               5

<210> SEQ ID NO 4
<211> LENGTH: 8
<212> TYPE: PRT
<213> ORGANISM: Artificial Sequence
<220> FEATURE:
<223> OTHER INFORMATION: kinase substrates

<400> SEQUENCE: 4

Met Asn Met Ser Pro Val Gly Asp
 1               5

<210> SEQ ID NO 5
<211> LENGTH: 16
<212> TYPE: PRT
<213> ORGANISM: Artificial Sequence
<220> FEATURE:
<223> OTHER INFORMATION: kinase substrates

<400> SEQUENCE: 5

Ala Ala Val Ala Leu Leu Pro Ala Val Leu Leu Ala Leu Leu Ala Pro
 1               5                  10                  15

<210> SEQ ID NO 6
<211> LENGTH: 4
<212> TYPE: PRT
<213> ORGANISM: Artificial Sequence
<220> FEATURE:
<223> OTHER INFORMATION: kinase substrates

<400> SEQUENCE: 6

Leu Arg Arg Ala
 1